ns Patent [19]

Curry et al.

[11] 4,323,466
[45] * Apr. 6, 1982

[54] GERMICIDE

[75] Inventors: Janet C. Curry, Palisade; Barbara H. Bory, Fairview, both of N.J.

[73] Assignee: Lever Brothers Company, New York, N.Y.

[*] Notice: The portion of the term of this patent subsequent to Jul. 6, 1996, has been disclaimed.

[21] Appl. No.: 177,302

[22] Filed: Aug. 11, 1980

Related U.S. Application Data

[60] Continuation of Ser. No. 926,777, Jul. 21, 1978, abandoned, which is a division of Ser. No. 308,064, Nov. 20, 1972, abandoned, which is a continuation-in-part of Ser. No. 72,527, Sep. 15, 1970, abandoned.

[51] Int. Cl.$^3$ .................. A61L 13/00; C11D 1/66; C11D 3/075; C11D 3/48
[52] U.S. Cl. .................. 252/106; 252/174.21; 424/232; 424/273 R; 424/340

[58] Field of Search .................. 252/106, 107, 174.21; 424/232, 273 R, 340

[56] References Cited

U.S. PATENT DOCUMENTS 2,215,862  9/1940  Waldman .................. 260/309
3,666,668  5/1972  Klausner .................. 252/90

OTHER PUBLICATIONS

J. Organic Chem., 12, pp. 577–586 (1947).
F D & C Report, T & G-3 (1969).

Primary Examiner—Dennis L. Albrecht
Attorney, Agent, or Firm—James J. Farrell; Melvin H. Kurtz

[57] ABSTRACT

Novel and improved antibacterial mixtures comprise a 2-alkylimidazoline and at least one bacteriostat from 3,4',5-tribromosalicylanilide, 4',5-dibromosalicylanilide and 2,4,4'-trichloro-2'-hydroxydiphenyl ether. These mixtures effectively destroy bacteria in a cleaning or laundering operation at room temperature and retard subsequent bacterial growth.

13 Claims, No Drawings

GERMICIDE

This application is a continuation of Ser. No. 926,777, filed July 21, 1978, now abandoned, which is a divisional of Ser. No. 308,064, filed Nov. 20, 1972, now abandoned, which is a continuation-in-part of Ser. No. 072,527, filed Sept. 15, 1970, now abandoned.

BACKGROUND OF THE INVENTION

1. Field of the Invention

The present invention relates to antibacterial mixtures comprising 2-alkylimidazolines wherein the alkyl group has about 9 to about 17 carbon atoms, and a bacteriostat. Preferably the bacteriostat is a compound selected from the group consisting of 3,4',5-tribromosalicylanilide 4',5-dibromosalicylanilide, or 2,4,4'-trichloro-2'-hydroxydiphenyl ether, or mixtures thereof. The compound 3,4',5-tribromosalicylanilide is referred to in portions of this specification as TBS; 4',5-dibromosalicylanilide is DBS, and 2,4,4'-trichloro-2'-hydroxydiphenyl ether is THDE.

The antibacterial mixtures have utilized for a variety of applications, such as sanitizing of walls and floors, as germicidal agents in toilet bars or in dishwashing compositions, and are especially useful in the washing of fabrics.

The components of the antibacterial mixtures of the present invention have the following structural formulas:

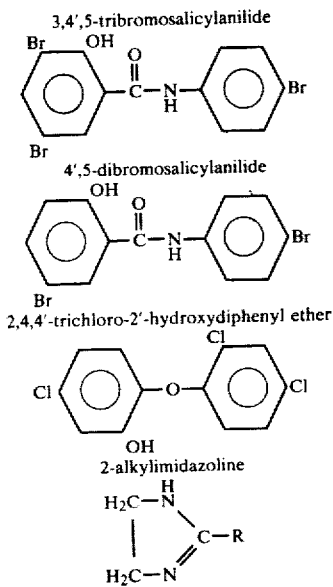

wherein R is an alkyl group having 9–17 carbon atoms.

It will be understood that the imidazolines referred to herein are the 2-substituted-2-imidazolines in accordance with the foregoing structure.

Numerous classes of bacteria survive automatic home laundry washing operations. Gram-negative bacteria have been found on washed clothes although these bacteria are largely destroyed when the clothes are dried. The Gram-positive bacteria, being more resistant to drying, are more frequently found on washed clothes than are the Gram-negatives. One of the more important Gram-positive bacteria, from the standpoint of public health, which has been found to persist on washed and dried clothes is *Staphylococcus aureus*. The antibacterial mixtures of the present invention are highly effective against the growth of this organism.

The need for eliminating bacteria on washed clothes or at least reducing bacteria to a minimum level is apparent. Formerly clothers were sanitized, i.e., bacteria reduced to a minimum level, by boiling in the wash operation. This procedure however does not impart bacteriostatic properties to the washed clothes, nor is it recommended for the case of present day synthetic or Permanent Press fabrics.

The word "sanitize" as used herein relates to the reduction of the number of bacteria on a fabric or other object to minimum levels as may as judged by public health requirements. The percent reduction may vary somewhat but generally is within the range of 95% to 99.999%, as set forth under "sanitizer" on page 7 of the booklet "Anti-Microbial Agents" (Interpretive Report) published by the Chemical Specialties Manufacturers Association, New York.

The present day practice of washing clothes in automatic washers is less effective for reducing bacterial level than the boiling method. The "hot water" setting seldom provides wash water having a temperature as high as 140° F. in any washing machine, and in view of the fact that it requires about 20 minutes to kill staphylococci by heat alone at 140° F. (the average home washing cycle is about 10 minutes) the usual washing operation cannot be expected to provide a sanitizing action. Also, some commercial detergent compositions are currently being formulated to wash in water at room temperature, which is usually about 68° F. to about 85° F. (about 20° C. to about 30° C.), and under these conditions the need for antibacterial action in the washing or rinsing operation is accentuated. Highly desirable too is a bacteriostatic action to lessen recontamination. Accordingly it has not been possible heretofore to sanitize clothing in a washing machine operation without resorting to the use of such antibacterial agents as quaternaries, hypochlorites, phenolics, or pine oil, or the use of relatively high levels of the organic halogen-containing antibacterial agents.

There are recognized drawbacks to the use of any of the above agents. Hypochlorites should not be used on silk or wool, and may bleach colored fabrics. Quaternaries are inactivated when used in the wash cycle with anionic detergents, while the phenolics and pine oil have odors that may be objectionable to some people. The high levels of the organic halogen-containing antibacterials which have been needed heretofore for both bactericidal and bacteriostatic action precluded their use on the basis of cost.

For a discussion of the bacterial problems encountered in home laundering, attention is directed to the seven-page brochure "Sanitation in Home Laundering" (Revised August, 1964) published by the United States Department of Agriculture, and available from the Superintendent of Documents.

2. The Prior Art

The desirability of incorporating a germicidal agent in detergent compositions has long been recognized, and much that has been written on the subject is found in the technical journals and in the patent literature. None of these however discloses the accomplishment set forth in the instant invention, i.e., the sanitizing of clothes in a single wash, even at relatively low temperatures, i.e., about 20° C. to about 40° C. Typical prior-art disclosures are discussed below.

Belgium Pat. No. 575,411, based on an application filed in the United States on Feb. 6, 1958, discloses the use of 0.01% to 2% of 3,3',4',5-tetrachlorosalicylanilide or related compounds, and additionally trichlorocarbanilide, and tetramethyl thiuram disulfide, as antibacterial agents in detergent compositions, useful at washing temperatures of 49° C.

Somewhat later the use of 1-hydroxy-2-pyridinethione compounds in detergent compositions was disclosed in South Africa Patent Application No. R61/1706 dated Sept. 26, 1961.

U.S. Pat. No. 3,428,736 issued on Feb. 18, 1969 describes synergistic bactericidal combinations comprising bis(3,5,6-trichloro-2-hydroxyphenyl)mothane (hexachlorophene) and a dibenz[be][1,4] oxiodinium salt, suitable for use in detergent compositions.

British Pat. No. 727,343 published in 1955 discloses and claims a broad group of halogenated salicylanilide compounds, and states that these compounds can be used with cleaning agents and other vehicles, for disinfectant purposes.

British Pat. No. 955,925, published in 1964 discloses that textile fibers can be made resistant to the growth of bacteria by washing the textile fibers with a detergent in which has been incorporated a mixture of 3,4',5-tribromosalicylanilide and one or more dibromosalicylanilides.

South Africa Pat. No. 68/3304 discloses that certain benzimidazoles retain their antimicrobial activity when added to cleaning agents.

The present invention permits substantially complete reduction in *Staphylococcus aureus* count on textile fabrics in one wash at room temperature or slightly higher, with residual antibacterial protection for extended periods. Prior art antimicrobial agents or mixtures thereof generally require elevated washing temperatures to obtain sanitizing and residual action. A typical teaching in this respect is found in British Pat. No. 955,925, which discloses a washing temperature of 49° C. (120° F.). Thus the present invention is timely, since it provides a means for obtaining good sanitizing and residual antimicrobial action in relatively cool water in conformity with the current practice of using room-temperature water in home laundering operations.

Typical also of prior washing conditions is the teaching of U.S. Pat. No. 3,211,607, wherein (in Example 4) there is described a washing test made at 40° C. and of 18 minutes' duration, using about 8%, basis detergent composition, (or 200 ppm, basis washing liquor) of a synergistic binary mixture of an amino imidazolidine and a trifluoromethyl dichlorocarbanilide. It is noteworthy that this mixture was tested at a longer contact time and at a much higher level of antibacterial mixture to obtain bactericidal action only, than required for the antibacterial mixture of the present invention to achieve both bactericidal and bacteriostatic activity.

SUMMARY OF THE INVENTION

It is an object of the present invention to provide an antibacterial composition having both bactericidal and bacteriostatic properties.

It is another object of the invention to provide an effective sanitizer having no objectionable side effects.

It is still another object of the present invention to provide a means for destroying bacteria on clothing.

It is a further object of the invention to provide an antibacterial mixture which, when used with a detergent in the warm cycle at room temperature or slightly higher, sanitizes fabrics and the interior surfaces of the washing machine in a single wash, and in addition, provides bacteriostatic protection to retard subsequent contamination.

These and other objects of the invention are accomplished by providing an antibacterial mixture comprising a 2-alkyl-2-imidazoline compound having about 9 to 17 carbon atoms, suitably 11-15 carbon atoms, and preferably 13 carbon atoms, in the alkyl group, along with one or more bacteriostats preferably 4',5-dibromosalicylanilide, 3,4',5-tribromosalicylanilide, 2,4,4'-trichloro-2'-hydroxydiphenyl ether, or mixtures thereof.

In a more specific application of the invention comprising the washing of fabrics, the aforementioned objects are accomplished by the incorporation of an antibacterial mixture of the invention in the washing solution or rinse water, or in the detergent used in the washing operation.

The antimicrobial mixtures of the present invention may be used in any compatible base. The may be employed for example in a fabric softener composition, a shampoo, an aerosol spray composition, a dentifrice, a detergent composition, a toilet bar, etc. For greater ease of handling in instances where it may be desired to add the antibacterial mixture separately to the washing machine in a washing operation, or if it is desired to formulate an aerosol product, the compatible base may be an inert diluent substance. The inert diluent substance may be a liquid such as water or alcohol, or a mixture thereof, or may be a solid in pulverulent or compressed form, such as sodium sulfate, sodium chloride, starch, sodium tripolyphosphate, etc. A preferred base is a compatible detergent base, particularly a nonionic detergent base. An anionic base is less preferred in view of the potentially cationic character of the imidazoline, and in view of the possibility that some combinations of anionic detergent and a 2-alkylimidazoline may result in inoperability of the germicidal mixture.

The percentage levels of the antibacterial mixtures in the compatible base will vary, depending upon the nature of the base and the use to which it is put. In general the percentage levels of the antibacterial mixtures will be such that there is sufficient for antibacterial effectiveness when the compatible base is employed at its normal or recommended use level.

Normal or recommended use concentration of particulate detergents is generally recognized as about 1 cupful for each 17 gallons of water. Due to variations in usage level by the consumer and to variations in specific gravity of the particulate detergent, levels of the detergent composition in the wash water of about 0.1% to about 0.3% are commonly employed.

The combination of a 2-alkylimidazoline and a bacteriostat has a two-fold advantage. The bactericidal action of the 2-alkylimidazoline is improved so that economical levels provide acceptable bactericidal action in one wash at room temperature as demonstrated in Table IV, while at the same time the substantivity of the bacteriostats is improved by the imidazoline compounds so that recontamination after washing is lessened, as shown in column 5 of Table III.

Of particular value is the finding the good bactericidal and bacteriostatic action is provided on cloth by a single 10-15 minute wash at temperatures between about 20° C. and about 40° C. through the use of a detergent composition having the antibacterial agents present within the proportions set forth above.

In one embodiment of the invention there is provided an antibacterial sanitizing composition effective to destroy at least 99.9% of S. Aureus cells during a contact time of about 10 to 15 minutes, at a temperature between about 25° C. to 40° C. As shown in Table IV, most of the antibacterial mixtures within the present invention have an effective sanitizing action in 10 minutes or less. The aforesaid composition may be binary and may exist in the form of a dry-appearing powder. The antibacterial sanitizing composition comprises a mixture of 2-alkylimidazoline wherein the alkyl group has 9-17 carbon atoms and at least one bacteriostatic halogenated compound selected from the group consisting of 4',5-dibromosalicylanilide, 3,4',5-tribromosalicylanilide, 2,4,4'-trichloro-2'-hydroxydiphenyl ether. The bacteriostatic halogenated compound is present in the mixture in the ratio of about 0.01 to about 2 parts, and preferably about 0.01 to about 1 part, for each part of the 2-alkylimidazoline. The binary mixtures have good sanitizing action in contrast to the substantial absence of sanitizing action of the imidazoline or the bacteriostats alone at advantageously low percentage levels, as shown in Table IV.

In a second embodiment of the invention there is provided an antibacterial detergent composition having bactericidal properties and being effective to destroy at least 99.9% of S. aureus cells during a contact time of about 10-15 minutes, at washing concentrations at a temperature of about 25° C. to about 40° C., comprising a binary mixture of (a) a 2-alkylimidazoline having an alkyl group of 9-17 carbon atoms, and (b) a bacteriostatic halogenated compound selected from the group consisting of 4',5-dibromosalicylanilide, 3,4',5-tribromosalicylanilide, and 2,4,4'-trichloro-2'-hydroxydiphenyl ether, and mixtures thereof, in a compatible detergent base. In the binary mixture, the 2-alkylimidazoline is present in proportions of about 0.5% to about 1.5%, preferably about 0.75% to about 1.25%, and the bacteriostatic halogenated compound is present in proportions of about 0.01% to about 10%, preferably about 0.01% to about 1%. The percentages are by weight of the compatible detergent base.

For example a detergent composition may contain 0.5% by weight of a 2-alkyl-2-imidazoline of the invention, along with 1% of one or a mixture of the bacteriostats, as shown in sample numbers 16-18 of Table IV, or the detergent composition may contain 1% of a 2-alkyl-2-imidazoline with 0.01% of one or a mixture of the bacteriostats as exemplified in sample numbers 31-33 of Table IV. These examples illustrate the effectiveness of ratios of bacteriostatic halogenated compound to imidazoline from 0.01 part by weight of 2 parts by weight of bacteriostat for each part by weight of imidazoline.

A third, and preferred embodiment contemplates an antibacterial composition having both bactericidal and bacteriostatic properties, and being effective to destroy at least 99.9% S. aureus cells during a contact time of about 10-15 minutes at 25° C. to 40° C. and being capable of simultaneously imparting good residual bacteriostatic action against recontamination under conditions wherein the composition is used at normal or recommended use concentrations, comprising a ternary mixture of (a) a 2-alkylimidazoline having an alkyl group of 9-17 carbon atoms, (b) a halogenated salicylanilide selected from the group consisting of 4',5-dioromosalicylanilide and 3,4',5-tribromosalicylanilide, and (c) a 2,4,4'-trichloro-2'-hydroxydiphenyl ether. This composition is particularly effective in the washing of fabrics. The halogenated salicylanilide is present in proportions of about 0.005 to about 0.4 part, preferably 0.01 to 1 part, and the 2,4,4'-trichloro-2'-hydroxydiphenyl ether is present in proportions of about 0.005 to about 0.03 part, preferably about 0.02 to 0.03 part, for each 0.5 to 5 parts of the 2-alkylimidazoline, by weight.

A fourth and more preferred embodiment of the instant invention includes an antibacterial detergent composition having both bactericidal and bacteriostatic properties, and being effective to destroy at least 99.9% of S. aureus cells during a contact time of about 10-15 minutes, and being capable of imparting good residual bacteriostatic action to fabrics against recontamination at washing concentrations in about 10-15 minutes at a temperature of about 25° C. to about 40° C. comprising a ternary mixture of (a) a 2-alkylimidazoline having an alkyl group of 9-17 carbon atoms, (b) a halogenated salicylanilide selected from the group consisting of 4',5-dibromosalicylanilide and 3,4',5-tribromosalicylanilide, and (c) 2,4,4'-trichloro-2'-hydroxydiphenyl ether, in a compatible detergent base. The 2-alkylimidazoline is present in the ternary mixture in proportions of about 0.5% to about 5%, preferably about 1% to about 2%, the halogenated salicylanilide is present in proportions of about 0.005% to about 0.4%, preferably about 0.01% to about 0.02%, and the 2,4,4'-trichloro-2'-hydroxydiphenyl ether is present in proportions of about 0.005% to about 0.03%, preferably about 0.02% to about 0.03%. The percentages are by weight of the compatible detergent base.

In fabric softeners, the percentage of total antibacterial agent varies from about 0.5% to about 5%. When admixed with an inert diluent, the percentage of total antibacterial agent varies widely, and may range from about 1% to about 99% in the case of a solid diluent, and from about 0.05 to about 15% in the case of a liquid diluent or aerosol spray.

The present invention also contemplates a process for sanitizing a fabric in a single contact period comprising contacting said fabric having thereon S. aureus cells with a mixture of a 2-alkylimidazoline wherein the alkyl group has 9-17 carbon atoms and a bacteriostatic halogenated compound selected from the group consisting of 4',5-dibromosalicylanilide, 3,4'-5-tribromosalicylanilide, 2,4,4'-trichloro-2'-hydroxydiphenyl ether and mixtures thereof.

In particular the process contemplates the use of the antibacterial mixtures in aqueous solution, preferably within the pH range of about 9 to about 11.

The concentration of 2-alkylimidazoline in the wash or rinsing solution may be from about 10 ppm to about 60 ppm, preferably about 15 ppm to about 40 ppm, and the concentration of the bacteriostatic halogenated compound may be from about 0.1 ppm to about 40 ppm, preferably about 0.4 ppm to about 30 ppm, by weight of the wash or rinse solution.

In commercial practice, the high cost of the aforementioned bacteriostats preclude their use in any but very low levels, and in fact it is a feature of the invention that only very small percentages of the relatively expensive bacteriostats need be used. In order that the germicidal mixture or a detergent containing it may be manufactured at a cost within a resonable range so that it may be made available to satisfy a consumer demand, it is especially preferred to use about 1% of the imidazoline and about 0.01% of the halogenated salicylanilide, and about 0.03% of the hydroxydiphenyl ether, by weight of the detergent composition. When used in spray-dried detergent compositions the antibacterial agents may be added to the crutcher slurry, or may be dissolved in a perfume or colorant solution and sprayed onto a bed of spray-dried powder. The agents may be dissolved in a solvent for use on hard surfaces or for the separate addition to the wash or rinse cycle during laundering.

The antibacterial mixture of this invention is particularly useful when employed in the presence of a detergent composition wherein the surfactant is of nonionic character, i.e., when the detergent base comprises as the active detergent a nonionic surface-active substance. The species of nonionic surfactant used is immaterial in obtaining the benefits of the invention, and the selection of the nonionic will be made on the basis of desired performance with respect to detergency, foaming, processing characteristics, etc.

An important class of nonionics comprise organic compounds found by condensing ethylene oxide with a hydrophobic base. The proportion of ethylene oxide may range from about 3 to about 30 or more molar proportions per mole of hydrophobic base, usually about 5 to about 20. Appropriate hydrophobic bases are:

(1) primary or secondary alcohols which are alkanols or alkenols (monohydroxyalkanes or -alkenes) having about 8 to about 22 carbon atoms, (2) alkane- or alkenediols having about 8 to about 22 carbon atoms, or their corresponding 1,2-epoxy compounds, (3) aliphatic monocarboxylic acids (alkanoic or alkenoic acids) having about 8 to about 22 carbon atoms, (4) alkyl mercaptans having about 8 to about 22 carbon atoms, (5) alkyl phenols having from about 6 to about 15 carbon atoms in the alkyl group.

(6) polypropylene oxide having a molecular weight of about 600 to about 2500, and (7) condensation product of ethylene diamine and propylene oxide, having a molecular weight of about 2500 to about 3000.

Examples of nonionic surfactants useful in detergent compositions into which the antibacterial mixtures can be incorporated are:

(a) alkyloxypolyoxyethylene ethanols

These are formed by condensing long-chain alkanols of alkenols having 8–22 carbon atoms with about 5–30 molar proportions of ethylene oxide. Of particular interest are the compounds wherein the alkyloxy portion has 10–14 carbon atoms and the polyoxyethylene ethanol portion comprises about 8–20 oxyethylene units.

(b) alkanoyloxypolyoxyethylene ethanols

These are esters which may be formed by condensing alkanoic or alkenoic acids with ethylene oxide, or by reacting an alkanoic or alkenoic acid with a previously prepared polyethylene glycol. The acids may have from about 8 to about 22 carbon atoms and the proportion of ethylene oxide may be from about 5 to about 30 moles per mole of acid. Preferably the alkanoic and alkenoic acids from which the nonionic surfactant is prepared have about 10 to about 18 carbon atoms, and may be a mixture derived for example from coconut oil or tallow. The proportion of ethylene oxide is preferably within the range of about 8 to 16 moles per mole of acid.

The alcohols or acids listed above under (a) or (b) may be branched or straight chain, and may be derived from natural fats or may be synthetically prepared.

(c) alkylthiopolyoxyethylene ethanols

These may be prepared by reacting alkyl mercaptans with ethylene oxide. Useful compounds are within the chain-length ranges described for the alkanolethylene oxide condensates described under (a) above.

(d) alkylphenoxypolyoxyethylene ethanols

These may be prepared by reacting an alkylphenol with ethylene oxide. The alkyl group may have from about 6 to about 15 carbon atoms in either a straight or branched chain configuration, and the proportions of ethylene oxide may be from about 5 to 25 moles per mole of alkylphenol. Preferably the alkyl group contains from about 9 to about 12 carbon atoms and the proportion of ethylene oxide is preferably from about 6 to about 12 moles per mole of alkylphenol. The alkyl substituent may be derived from polymerized propylene, diisobutylene, octene, dodecene or nonene, for example.

(e) compounds formed by the simultaneous polymerization of propylene oxide and ethylene oxide, and containing randomly positioned oxypropylene and oxyethylene groups. These and related compounds are described in U.S. Pat. Nos. 2,979,528; 3,036,118; 3,022,335; 3,036,130; and 3,048,548.

(f) the polyoxyethylene-polyoxypropylene condensates sold under the trade name of "Pluronic"

These compounds are formed by condensing ethylene oxide with a hydrophobic base formed by the condensation of propylene oxide with propylene glycol to a molecular weight of about 600 to 2500. The proportion of ethylene oxide can range from about 10% to about 90%, by weight of the total condensation product. The Pluronics are described in U.S. Pat. Nos. 2,674,619 and 2,677,700.

(g) The nonionic surfactants prepared by first reacting propylene oxide with ethylene diamine to form a hydrophobic portion, and then condensing therewith ethylene oxide. Suitable compounds of this class may have a hydrophobic portion with a molecular weight of about 5,000 to about 11,000, and contain from about 40% to about 80% by weight of ethylene oxide. These and similar compounds are described in U.S. Pat. No. 2,979,528.

(h) 2-hydroxyalkyl ethers of ethylene glycol or glycerol, prepared by reacting ethylene glycol or glycerol with a 1,2-epoxyalkane having about 8 to about 18 carbon atoms, as disclosed in U.S. Pat. No. 3,427,248.

In a nonionic detergent composition the antibacterial mixtures of the present invention provide a quickkilling action against most bacteria commonly found on clothing, and also provide a substantive bacteriostatic action for prolonged protection. The usual detergent builders and adjuvants may be present. Builders may be for example alkali metal tripolyphosphates, pyrophosphates, orthophosphates, carbonates, bicarbonates, borates, perborates, nitrilotriacetates, ethylenediamine tetraacetates, silicates, etc.

Other adjuvants may be sodium sulfate, colorants, perfumes, hydrotropes, anticaking agents, suds boosters, optical brighteners, etc.

Antibacterial agents other than those set forth as being within this invention will not normally be needed, although they may be used so long as they do not interfere with the basic and novel characteristics of the instant invention.

TEST PROCEDURES

The Bactericidal Contact Time Test

This test is a modification of the test described by F. W. Barber in an article titled "Laboratory Evaluation of Cleaner-Sanitizers for Use on Dairy Farms", published in the Journal of Milk and Food Technology, Volume 12, pages 257–266 (1949).

The modification as used to obtain the results set forth hereinafter is conducted under conditions simulating the adverse conditions as to water hardness and soil usually found in home-laundering operations.

Prepare reaction mixtures in medication tubes by adding 1 ml. of a 1.5% solution of a nonionic-based detergent composition to 8 ml. of calcium hardness water at 250 ppm calculated as $CaCO_3$. Add 1 ml. of a 0.2% soil suspension of a mixture of 85 parts vacuum cleaner dust and 15 parts artifical sebum having the following composition:

|  |  |
| --- | --- |
| stearic acid | 31.4% |
| winterized cottonseed oil | 29.0% |
| $C_8$—$C_{10}$ fatty acids | 3.3% |
| lauryl alcohol | 15.3% |
| n-hexane | 21.0% |

Add a 0.5 gm. swatch of cotton fabric to provide a 1:20 fabric-to-water ratio. Prepare one 10-ml. distilled water tube for temperature control. Place the tubes in a water bath at 40° C. and hold until the temperature of the control tube reaches 40° C.

With the start of a stopwatch add 0.1 ml. of a 24-hour AATCC Nutrient Broth Culture of $10^8$ S. aureus per ml. which has been diluted 1:1 with sterile 0.1% peptone water. This results in approximately $3 \times 10^6$ S. aureus per ml. of test solution.

Withdraw 0.01 ml. loop samples at the desired contact times and transfer to oval tubes containing 5 ml. sterile Microinoculum Agar, held molten in a 48° C. water bath. Mix gently and slant in a rack.

To determine initial count employed, dilute culture suspension $10^{-3}$ and add 0.1 ml. to 9 ml. sterile distilled water in a medication tube. Transfer 0.01 ml. loop samples (at least 3) to oval tubes and slant as for samples.

After hardening of the sample agar mixtures, invert rack of tubes and incubate at 37° C. overnight.

Record tube colony counts and relate to control for endpoint; i.e. any tube in test series containing same or lower numbers of colonies as average control count = 99.9% kill.

Reults are reported as time (minutes) to effect 99.9% kill of $10^6$ bacteria/ml.

Seeded Agar Plate Test

This test is based on AATCC Test No. 90.

AATCC Nutrient Agar is seeded at 1% with AATCC Nutrient Broth Culture of S. aureus. The agar is allowed to harden.

Swatches of cloth to be tested are carefully applied to the surface of the agar plates, which are then incubated overnight at 35° C. After overnight incubation zones of inhibition are measured. If no zones (surrounding the cloth) are evident, the swatch is removed and the area of contact on the agar examined microscopically.

Inhibition of the seed organism in the contact area is graded and reported as follows:

0 = no inhibition
1 = slight inhibition
2 = moderate inhibition
3 = strong inhibition
4 = complete inhibition with or without a zone of inhibition surrounding cloth.

Inoculated Swatch Test

This test is a modification of the test described by H. Quinn in "Applied Microbiology", Volume 10, p 74 (1962) and by W. D. Haskins et al. in "Chemical Specialties Mfgrs. Association Proceedings", p 140. In the modification used for testing the compositions of the present invention a volume of 22 ml. of Nutrient Agar and 15 ppm of triphenyl tetrazolium chloride are placed in a large Petri dish and allowed to harden. The triphenyl tetrazolium chloride provides contrast between colonies (red) and fabric (white). A swatch of cloth to be tested is carefully placed on the agar surface. The cloth is then inoculated so as to provide 50–100 S. aureus cells per swatch, and allowed to incubate overnight (16–18 hours). If the cloth has been inoculated in a washing or rinsing operation, no further inoculum is used. The growth of bacteria on the cloth is determined by comparing the colony count with that of a similar swatch known to contain no antibacterial agent. The extent of bacterial growth on a test cloth, or the extent of inhibition of bacterial growth on a test cloth previously treated with a bacteriostat is translated to grade numbers 0–4 having the following meaning:

0 = no bacteriostatic activity (similar to control in size and number of colonies)
1 = slight bacteriostatic activity (less than 50% reduction)
2 = moderate bacteriostatic activity (50% to 90% reduction)
3 = strong bacteriostatic activity (between 90% and 100% reduction)
4 = zero count (100% reduction).

The Laundry Simulator

The apparatus referred to as a Laundry Simulator is simply a device for vertically rotating and tumbling eight 1-pint screw-capped mason jars around a horizontal axis. The apparatus comprises a rotatable horizontal rod concentrically affixed at the center of a vertically disposed 8-inch diameter circular metal plate, around the periphery of which is constructed eight flat square 3"×3" supports defining an octagonal configuration, the plane on each support being normal to a radius of the circular plate. On the outer surface of each support is affixed the screw cap of a one-pint mason jar, so placed that when the jar is attached, it is disposed radially with a capped end toward the center of the circular plate. The overall diameter when opposing jars are in place is 18 inches. For the tests described herein the jars were rotated at a speed of 44 r.p.m.

A one-jar tumbling device from which the above-described equipment evolved is described in AATCC Technical Manual 1968, page B-157 (Test AATCC 70B-1967).

The following examples will lead to a more complete understanding of the present invention. These examples are for illustrative purposes only, and are not intended to be construed as defining the limits of the scope of the invention.

EXAMPLE 1

The bactericidal effectiveness of a ternary antibacterial mixture within our invention is shown by the following:

Two hundred ml. of a sterile solution of a detergent-/antibacterial mixture in distilled water is prepared containing the following and placed in one of the 1-pint containers of the Laundry Simulator:

|  | Concn. in Wash Liquor |  |
|---|---|---|
| (a)0.5 gm. commercial detergent composition | 0.25% |  |
| (b)0.0862 gm. NaHCO$_3$ | } 250 ppm |  |
| (b)0.0570 gm. CaCl$_2$ |  |  |
| (c)0.04 gm. soil | 200 ppm soil |  |
| 0.8% 2-tridecyl imidazoline | 20 ppm |  |
| (c)0.01% of a 50:50 mixture of 3,4′,5-tribromosalicylanilide and 4′,5-dibromosalicylanilide (PBS) | 0.25 ppm |  |
| (d)0.03% 2,4,4′-trichloro-2′-hydroxydiphenyl ether (THDE) | 0.75 ppm |  |

(a)The composition contains a nonionic surfactant and tetrapotassium pyrophosphate.
(b)The NaHCO$_3$ and CaCl$_2$ are predissolved. The proportions shown provide 250 ppm calcium hardness calculated as CaCO$_3$.
(c)A mixture of 85% vacuum cleaner dust and 15% artificial sebum mixture having the composition described under "Test Procedures".
(d)Percentages are by weight of the detergent composition.

Thirty pieces of cotton cloth each measuring 1¼ inches by 4 inches in size and weighing a total of 10 grams are placed in the solution, followed by 2 ml. of an overnight broth culture of S. aureus to provide a bacterial count of $10^6$ per ml. of wash liquor. The broth culture is plated to determine the actual count.

Using the Laundry Simulator procedure described hereinbefore, 1 ml. of the water is removed after a 10-minute wash at room temperature, and also after each of two 5-minute rinses, placed in 10 ml. of sterile Letheen Broth, and plated in Trypticase Soy Letheen Agar, and plate counts determined after a 48-hour incubation period. By comparison with an initial count, the ternary antibacterial composition of Example 1 effects a 99.9997% kill.

EXAMPLE 2

To illustrate that the antibacterial compositions of the present invention have residual bacteriostatic properties, reference is made to the following experiment.

A swatch of the cloth, after washing and rinsing in accordance with Example 1, is air dried and placed on sterile nutrient agar containing 15 ppm triphenyl tetrazolium chloride. After overnight incubation the red colonies which develop are counted by a method similar to that described in the Haskins article mentioned hereinbefore under "Test Procedures—Inoculated Swatch Test". The extent of development of red colonies is a measure of bacteria picked up from the inoculated wash water. In the test referred to above, 30 red colonies develop. In contrast, the red colonies which develop in a control test carried out in the same manner but with omission of the antibacterial agents are too numerous to count.

A second swatch of the cloth washed with the composition of Example 1, is tested for residual antibacterial activity by the Seeded Agar Plate Test described hereinbefore. The cloth shows a positive zone of inhibition, that is, no bacterial growth is observed on the agar in contact with the cloth or on an area immediately surrounding the cloth. By contrast, cloth washed in the above-mentioned control test has no inhibiting action.

EXAMPLE 3

The colony counts shown below demonstrate the improved bacteriostatic action of the antibacterial mixtures of the invention.

Cotton cloth is washed in the Laundry Simulator in the manner described in Example 1, except that no bacteria are added to the wash water.

Within the conditions of the Inoculated Swatch Test described hereinbefore, a known number (about 50 to 100) of S. aureus cells are placed directly on a 1⅛ inch diameter piece of a washed swatch after 4 washings and an air drying at 37° C., the swatch having been first placed in contact with the surface of a plate containing sterile nutrient agar with 15 ppm triphenyl tetrazoline chloride. After incubation overnight at 35° C., the red colonies which develop can be counted.

By means of the above test procedure, 2-tridecyl imidazoline, PBS, and THDE are tested in a 0.25% solution of a nonionic-based built detergent composition. The percentage figures are based on the whole detergent composition.

| Code | % Imidaxoline | % PBS | % THDE | Colony Count |
|---|---|---|---|---|
| A | 1.0 | — | — | 63 |
| B | 1.0 | 0.02 | — | 48 |
| C | 1.0 | — | 0.02 | 3 |
| D | 1.0 | 0.01 | 0.01 | 9 |
| E | — | 0.02 | — | 71 |
| F | — | — | 0.02 | 61 |

The foregoing colony counts show that by combining a 2-alkylimidazoline with 2,4,4′-trichloro-2′-hydroxydiphenyl ether (THDE), either alone or with PBS, all at relatively low concentrations, excellent inhibition of bacterial growth is achieved.

EXAMPLE 4

This illustrates the incorporation of the antibacterial agents of this invention in a detergent composition by spraying a solution of the agents onto a bed of a dried particulated detergent powder. To prepare the detergent powder, the following components are mixed together:

|  | % |
|---|---|
| *Nonionic detergent | 15.0 |
| Sodium tripolyphosphate, Type I | 50.0 |
| Na$_2$SO$_4$ | 20.0 |
| Water | 15.0 |
|  | 100.0 |

*Condensate of an acrylic aliphatic alcohol having 14–15 carbon atoms and about 11 moles ethylene oxide The foregoing components are mixed together as a slurry in a quantity to provide 1,000 gms. of the above formula, allowed to crystallize and broken up into a particulated form. To 100 gms. of the particles are added, by spraying thereon, 5 gm. of the following antibacterial solution:

| Water | 45 parts |
|---|---|
| Ethyl alcohol | 44.6 parts |

-continued

| 2-tridecyl imidazoline | 10 parts |
| 3,4',5-tribromosalicylanilide | 0.2 parts |
| THDE | 0.2 parts |

The antibacterial solution is prepared by mixing together the antibacterial agents in dry form in a beaker, and adding thereto the aforementioned solvents.

EXAMPLE 5

The following compositions shown in Table II are within the scope of the invention.

TABLE II

| | Percent by Weight | | | | | | | |
|---|---|---|---|---|---|---|---|---|
| | 1 | 2 | 3 | 4 | 5 | 6 | 7 | 8 |
| Lauric acid . 16 E.O. | 15 | — | — | — | — | — | — | — |
| Dodecanol . 10 E.O. | — | 15 | — | — | 15.0 | — | 12 | — |
| Dodecylphenol . 6 E.O. | — | — | 15 | — | — | — | — | 12 |
| Dodecane-1,2-diol . 7 E.O. | — | — | — | 15 | — | — | — | — |
| Trisodium nitrilotriacetate | — | — | — | — | 30.0 | — | — | — |
| Tetrapotassium pyrophosphate | — | 40 | 40 | — | — | — | — | — |
| Sodium tripolyphosphate | — | — | — | 10 | — | — | — | — |
| 2-undecyl imidazoline | 2 | — | 0.5 | — | — | — | 1 | 1 |
| 2-tridecyl imidazoline | — | — | — | — | 1.0 | — | — | — |
| 2-pentadecyl imidazoline | — | 2 | — | 0.5 | — | 1 | — | — |
| 4',5-dibromosalicylanilide | 0.01 | — | — | — | 0.005 | 0.01 | 0.4 | — |
| 3,4',5-tribromosalicylanilide | — | 0.01 | — | 2 | 0.005 | — | — | — |
| 2,4,4'-trichloro-2'-hydroxy-diphenyl ether | — | — | 2 | — | 0.03 | — | — | 0.4 |
| Water | 82.99 | 42.99 | 42.5 | 72.5 | 53.96 | 98.99 | 86.6 | 86.6 |

"E.O." preceded by a number indicates average molar proportions of ethylene oxide.

EXAMPLE 6

Solutions of a 0.2% nonionic detergent composition by weight are prepared containing in addition the antibacterial compounds listed in Table I. To each solution is added one piece of cotton cloth, measuring 12"×12" and weighing 10 grams. The cloth is given one 10-minute wash at room temperature (about 25° C.) then rinsed twice with successive 200-ml. portions of tap water, using the Laundry Simulator procedure described hereinabove.

Circular swatches 1⅛ inches in diameter are cut from the fabric and applied to an agar plate seeded with 1% S. aureus, in accordance with the Seeded Agar Plate Test described hereinbefore. The degree of inhibition of bacterial growth in the agar is indicative of the residual bacteriostatic action of the antibacterial agents on the cloth. A grading of 0 indicates no bacteriostatic activity. A grading of 4 indicates complete inhibition of the growth of the test organism. Grades 1-3 are assigned to progressively smaller intermediate growths. The results of the Seeded Agar Plate Test are shown in column 4 of Table III, below.

Other swatches of the same size are cut from the washed and rinsed cloth and placed on a sterile agar plate in accordance with the Inoculated Swatch Test described elsewhere herein. The swatches are inoculated with 50-100 bacteria each. After incubating overnight, a count is made of the number of bacteria on the cloth, and the extent of inhibition of growth determined and recorded by the numbers 0-4, which have the same meaning as above. This test is designed to show the effect of the antibacterial agents of the invention in providing a bacteriostatic finish to cloth and in preventing recontamination. The results of the Inoculated Swatch Test are shown in the last column of Table III.

The figures in parentheses are the results of a repeat test for verification.

A comparison of Sample Nos. 1, 14, and 18 in Table III shows that 1% tridecyl imidazoline, having no bacteriostatic activity itself, enhances the bacteriostatic activity of a mixture of 0.01% PSB[a] and 0.03% THDE[b].

[a],[b]See footnote, Table III.

TABLE III

BACTERIOSTATIC EFFECTIVENESS BY THE SEEDED AGAR PLATE TEST AND BY THE INOCULATED SWATCH TEST

Percent Antibacterial Agent,

| | Whole Composition Basis. | | | Inhibition Grade | |
|---|---|---|---|---|---|
| Sample No. | Tridecyl Imidazoline | PBS[a] | THDE[b] | Seeded Agar | Inoculated Swatch |
| 1 | 1 | 0 | 0 | 0 | — |
| 2 | 5 | 0 | 0 | 2.5 | — |
| 3 | 10 | 0 | 0 | 4 | — |
| 4 | 1 | 0.01 | 0.03 | 4(4) | 4 |
| 5 | 1 | 0.015 | 0.025 | 3 | — |
| 6 | 1 | 0.02 | 0.03 | 4(4) | 4 |
| 7 | 1 | 0.025 | 0.035 | 4 | — |
| 8 | 1 | 0.03 | 0.03 | 4(4) | 4 |
| 9 | 1 | 0.04 | 0.03 | 4(4) | 4 |
| 10 | 1 | 0.05 | 0.02 | 2.5(2) | 4 |
| 11 | 1 | 0.1 | 0.03 | 3 | 4 |
| 12 | 1 | 0.3 | 0.03 | 3 | 4 |
| 13 | 1 | 0.4 | 0.03 | 3 | 4 |
| 14 | 1 | 0.01 | 0 | 0 | 1 |
| 15 | 1 | 0.4 | 0 | 2 | 4 |
| 16 | 1 | 0 | 0.01 | 0 | 4 |
| 17 | 1 | 0 | 0.02 | 2 | 4 |
| 18 | 1 | 0 | 0.03 | 3 | 4 |
| 19 | 1 | 0 | 0.04 | 4 | 4 |

[a] = about equal parts by weight of 4',5-dibromosalicylanilide and 3,4',5-tribromosalicylanilide
[b] = 2,4,4'-trichloro-2'-hydroxydiphenyl ether
— = not tested

EXAMPLE 7

This experiment demonstrates that good sanitizing conditions are provided by a nonionic detergent composition containing from about 0.5% to about 1% of a 2-alkylimidazoline in combination with certain properties of the bacteriostats of the invention. Combinations of about 0.5% to about 1% of a 2-alkyl ($C_{11}$–$C_{15}$) imidazoline and as little as about 0.01% of 4',5-di-, or 3,4',5-tribromosalicylanilide or mixtures thereof with 2,4,4'-trichloro-2'-hydroxydiphenyl ether effect a minimum of a 99.9% kill of S. aureus in 15 minutes or less.

Combinations of the antibacterial agents of the present invention at several levels and ratios in 0.2% aqueous solutions of the detergent composition described in Example 4 are tested by the Bactericidal Contact Time Test, described elsewhere in this application.

The results of this experiment, shown in Table IV, also demonstrate that 2-tridecyl imidazoline at concentrations of 1% of less by weight of the detergent composition has no sanitizing power, that is, does not reduce bacteria to a safe level in 15 minutes. The results also demonstrate that the three bacteriostats tested, namely TBS, DBS, and THDE, which have no sanitizing action even at 10%, may be combined with the 2-tridecyl imidazoline to form a combination having good sanitizing action at total levels ranging from about 0.5% (Samples 11-15) to about 2% (Samples 36-38).

TABLE IV

BACTERICIDAL (SANITIZING) EFFECTIVENESS BY THE BACTERICIDAL CONTACT TIME TEST
Minutes to Effect a 99.9% Kill of *S. Aureus* at 40° C. in 0.2% Detergent

| Sample No. | % By Weight-Detergent Composition Basis | | | | Bactericidal Counts After Various Contact Times, Minutes (Initial Count = 2.6 × 10⁶/ml) | | | | | | | Minutes To Effect a 99.9% Kill |
|---|---|---|---|---|---|---|---|---|---|---|---|---|
| | C₁₃ Imid-azoline | TBS | DBS | THDE | 1 | 2 | 3 | 4 | 5 | 10 | 15 | |
| 1 | 0.1 | 0.01 | | | TNC | | | | | | TNC | >15 |
| 2 | 0.1 | | 0.01 | | TNC | | | | | | TNC | >15 |
| 3 | 0.1 | | | 0.01 | TNC | | | | | | TNC | >15 |
| 4 | 0.1 | 0.005 | | 0.005 | TNC | | | | | | TNC | >15 |
| 5 | 0.1 | | 0.005 | 0.005 | TNC | | | | | | TNC | >15 |
| 6 | 0.1 | 1 | | | TNC | | | | | | TNC | >15 |
| 7 | 0.1 | | 1 | | TNC | | | | | | TNC | >15 |
| 8 | 0.1 | | | 1 | TNC | | | | | | TNC | >15 |
| 9 | 0.1 | 0.5 | | 0.5 | TNC | | | | | | TNC | >15 |
| 10 | 0.1 | | 0.5 | 0.5 | TNC | | | | | | TNC | >15 |
| 11 | 0.5 | 0.01 | | | TNC | TNC | TNC | 62 | 20 | 2 | 0 | 5 |
| 12 | 0.5 | | 0.01 | | TNC | TNC | TNC | 50 | 36 | 5 | 0 | 5-10 |
| 13 | 0.5 | | | 0.01 | TNC | TNC | TNC | TNC | TNC | 31 | 7 | 5-10 |
| 14 | 0.5 | 0.005 | | 0.005 | TNC | TNC | TNC | TNC | 62 | 50 | 2 | 10-15 |
| 15 | 0.5 | | 0.005 | 0.005 | TNC | TNC | TNC | TNC | 39 | 9 | 2 | 5-10 |
| 16 | 0.5 | 1 | | | TNC | TNC | TNC | TNC | TNC | TNC | 28 | 10-15 |
| 17 | 0.5 | | 1 | | TNC | TNC | TNC | TNC | TNC | TNC | 36 | 10-15 |
| 18 | 0.5 | | | 1 | TNC | TNC | 51 | 40 | 35 | 1 | 0 | 5-10 |
| 19 | 0.5 | 0.5 | | 0.5 | TNC | TNC | TNC | 65 | 75 | 26 | 13 | 5-10 |
| 20 | 0.5 | | 0.5 | 0.5 | TNC | TNC | TNC | 75 | 52 | 10 | 0 | 5-10 |
| 21 | 0.75 | 0.01 | | | 52 | 80 | 17 | 11 | 3 | 0 | 0 | 3 |
| 22 | 0.75 | | 0.01 | | 55 | 68 | 40 | 14 | 16 | 26 | 0 | 4 |
| 23 | 0.75 | | | 0.01 | 50 | 60 | 33 | 13 | 4 | 0 | 0 | 4 |
| 24 | 0.75 | 0.005 | | 0.005 | TNC | 37 | 10 | 4 | 3 | 2 | 0 | 3 |
| 25 | 0.75 | | 0.005 | 0.005 | TNC | 40 | 33 | 30 | 11 | 0 | 0 | 4 |
| 26 | 0.75 | 1 | | | TNC | TNC | TNC | TNC | 62 | 15 | 6 | 5-10 |
| 27 | 0.75 | | 1 | | TNC | TNC | 20 | 13 | 10 | 0 | 0 | 3 |
| 28 | 0.75 | | | 1 | TNC | 52 | 29 | 28 | 22 | 7 | 0 | 3 |
| 29 | 0.75 | 0.5 | | 0.5 | TNC | 60 | 40 | 18 | 8 | 0 | 0 | 4 |
| 30 | 0.75 | | 0.5 | 0.5 | TNC | TNC | 17 | 10 | 6 | 0 | 0 | 3 |
| 31 | 1 | 0.01 | | | 72 | 26 | 5 | 1 | 0 | 0 | 0 | 2 |
| 32 | 1 | | 0.01 | | 42 | 4 | 3 | 0 | 0 | 0 | 0 | 2 |
| 33 | 1 | | | 0.01 | 23 | 4 | 0 | 0 | 0 | 0 | 0 | 1 |
| 34 | 1 | 0.005 | | 0.005 | 55 | 8 | 0 | 0 | 0 | 0 | 0 | 2 |
| 35 | 1 | | 0.005 | 0.005 | 75 | 50 | 22 | 8 | 1 | 0 | 0 | 3 |
| 36 | 1 | 1 | | | TNC | 60 | 13 | 10 | 2 | 0 | 0 | 3 |
| 37 | 1 | | 1 | | TNC | 24 | 3 | 2 | 0 | 0 | 0 | 2 |
| 38 | 1 | | | 1 | 32 | 13 | 1 | 2 | 0 | 0 | 0 | 2 |
| 39 | 1 | 0.5 | | 0.5 | TNC | 24 | 11 | 1 | 0 | 0 | 0 | 2 |
| 40 | 1 | | 0.5 | 0.5 | 44 | 16 | 3 | 0 | 0 | 0 | 0 | 2 |
| 41 | 0.1 | | | | TNC | | | | | | TNC | <15 |
| 42 | 0.5 | | | | TNC | | | | | | TNC | >15 |
| 43 | 0.75 | | | | TNC | | | | | | TNC | >15 |
| 44 | 1 | | | | TNC | TNC | TNC | TNC | TNC | TNC | 72 | >15 |
| 45 | 2 | | | | 11 | 1 | 0 | 0 | 0 | 0 | 0 | 1 |
| 46 | | 0.5 | | | TNC | | | | | | TNC | >15 |
| 47 | | 1 | | | TNC | | | | | | TNC | >15 |
| 48 | | 1.5 | | | TNC | | | | | | TNC | >15 |
| 49 | | 2 | | | TNC | | | | | | TNC | >15 |
| 50 | | 5 | | | TNC | | | | | | TNC | >15 |
| 51 | | 10 | | | TNC | | | | | | TNC | >15 |
| 52 | | | 0.5 | | TNC | | | | | | TNC | >15 |
| 53 | | | 1 | | TNC | | | | | | TNC | >15 |
| 54 | | | 1.5 | | TNC | | | | | | TNC | >15 |
| 55 | | | 2 | | TNC | | | | | | TNC | >15 |
| 56 | | | 5 | | TNC | | | | | | TNC | >15 |
| 57 | | | 10 | | TNC | | | | | | TNC | >15 |
| 58 | | | | 0.5 | TNC | | | | | | TNC | >15 |

TABLE IV-continued

BACTERICIDAL (SANITIZING) EFFECTIVENESS BY
THE BACTERICIDAL CONTACT TIME TEST
Minutes to Effect a 99.9% Kill of S. Aureus at 40° C. in 0.2% Detergent

| Sample No. | % By Weight-Detergent Composition Basis | | | | Bactericidal Counts After Various Contact Times, Minutes (Initial Count — 2.6 × 10⁶/ml) | | | | | | | Minutes To Effect a 99.9% Kill |
|---|---|---|---|---|---|---|---|---|---|---|---|---|
| | $C_{13}$ Imidazoline | TBS | DBS | THDE | 1 | 2 | 3 | 4 | 5 | 10 | 15 | |
| 59 | | | | 1 | TNC | | | | | | TNC | >15 |
| 60 | | | | 1.5 | TNC | | | | | | TNC | >15 |
| 61 | | | | 2 | TNC | | | | | | TNC | >15 |
| 62 | | | | 5 | TNC | | | | | | TNC | >15 |
| 63 | | | | 10 | TNC | TNC | TNC | TNC | TNC | 72 | 34 | >15 |

TNC = too numerous to count

EXAMPLE 8

This example demonstrates the operability of 2-alkylimidazoline having alkyl groups of chain lengths other than the $C_{13}$ chain length exemplified in previous examples. The utility of 2-alkylimidazolines having $C_9$, $C_{11}$, $C_{15}$ and $C_{17}$ alkyl groups is shown in Table V, below.

The tests are performed by washing swatches of cloth as described in Example 1, and testing for antibacterial activity on the cloth by the Seeded Agar Plate Test described elsewhere herein. In the washing operation, the washing solution contains 0.2% by weight of a detergent composition based on a nonionic detergent and sodium tripolyphosphate, and a ternary antibacterial mixture consisting of 1% 2-alkylimidazoline, 0.01% of PBS, which is a 50/50 mixture of 4',5-dibromosalicylanilide and 3,4',5-tribromosalicylanilide, and 0.03% of agent THDE, which is 2,4,4'-trichloro-2'-hydroxydiphenyl ether, the percentages of the antibacterial agents being by weight of the detergent composition.

TABLE V

| No. of Carbon Atoms in Alkyl Portion of 2-alkyl-imidazoline | Results of Seeded Agar Plate Test Grade |
|---|---|
| 9 | 4 |
| 11 | 4 |
| 15 | 4 |
| 17 | 3 |

In the foregoing tests, a zone of inhibition was observed on the agar surface surrounding the cloth swatch in the case of the $C_9$, $C_{11}$, and $C_{15}$ alkylimidazolines (grade 4). Inhibition was graded as "strong", or "grade 3" without a surrounding zone of inhibition, for the $C_{17}$ alkylimidazoline.

Although the utility of the antibacterial mixtures is set forth herein primarily in terms of activity during the washing of fabrics, it will be understood that the utility is not limited thereto, and that the antibacterial mixtures are contemplated for use in any application wherein they may find utility.

Having described the invention, the Examples of which as described hereinabove are illustrative and not intended to be limiting, we hereby set forth the manner in which we desire to claim the invention, the scope of which is to be limited only by the appended claims.

What is claimed is:

1. An antibacterial detergent composition having bactericidal properties and being effective to destroy at least 99.9% of S. aureus cells during a contact time of about 10-15 minutes at washing concentrations at a temperature of about 25° C. to about 40° C., comprising
  (a) a 2-alkyl-2-imidazoline having an alkyl group of 9-17 carbon atoms,
  (b) a bacteriostatic halogenated compound selected from the group consisting of 4',5-dibromosalicylanilide, 3,4',5-tribromosalicylanilide, and 2,4,4'-trichloro-2'-hydroxydiphenyl ether, and mixtures thereof, in a compatible detergent base, the weight ratio of (b) to (a) being from about 0.01:1 to about 2:1 by weight.

2. An antibacterial detergent composition in accordance with claim 1, wherein said detergent base comprises as the active detergent a nonionic surface-active substance.

3. An antibacterial detergent composition in accordance with claim 1 wherein said 2-alkyl-2-imidazoline is 2-tridecyl-2-imidazoline.

4. An antibacterial detergent composition in accordance with claim 1 wherein said 2-alkyl-2-imidazoline is present in proportions of about 0.5% to about 1.5%, and said bacteriostatic halogenated compound is present in proportions of about 0.01% to about 10%, said percentages being by weight of said compatible detergent base.

5. An antibacterial detergent composition in accordance with claim 1 wherein said 2-alkyl-2-imidazoline is present in proportions of about 0.75% to about 1.25%, and said bacteriostatic halogenated compound is present in proportions of about 0.01% to about 1%, said percentages being by weight of said compatible detergent base.

6. An antibacterial detergent composition having both bactericidal and bacteriostatic properties, and being effective to destroy at least 99.9% of S. aureus cells during a contact time of about 10-15 minutes, and being capable of imparting good residual bacteriostatic action to fabrics against recontamination at washing concentrations in about 10-15 minutes at a temperature of about 25° C. to about 40° C. comprising
  (a) a 2-alkyl-2-imidazoline having an alkyl group of 9-17 carbon atoms,
  (b) a halogenated salicylanilide selected from the group consisting of 4',5-dibromosalicylanilide and 3,4',5-tribromosalicylanilide, and
  (c) 2,4,4'-trichloro-2'-hydroxydiphenyl ether in a compatible detergent base, said halogenated salicylanilide being present in proportions of about 0.005 to about 0.4 part, and said 2,4,4'-trichloro-2'-hydroxydiphenyl ether being present in proportions of about 0.005 to about 0.03 part, for each 0.5 to 5 parts of said 2-alkyl-2-imidazoline, by weight.

7. An antibacterial detergent composition in accordance with claim 6, wherein said detergent base comprises as the active detergent a nonionic surface-active substance.

8. An antibacterial detergent composition in accordance with claim 6 wherein said 2-alkyl-imidazoline is 2-tridecyl-2-imidazoline.

9. An antibacterial detergent composition in accordance with claim 6 wherein said 2-alkyl-2-imidazoline is present in proportions of about 0.5% to about 5%, said halogenated salicylanilide is present in proportions of about 0.005% to about 0.4%, and said 2,4,4'-trichloro-2-hydroxydiphenyl ether is present in proportions of about 0.005% to about 0.03%, said percentages being by weight of said compatible detergent base.

10. An antibacterial detergent composition in accordance with claim 6 wherein said 2-alkyl-2-imidazoline is present in proportions of about 1% to about 2%, said halogenated salicylanilide is present in proportions of about 0.01% to about 0.02%, and said 2,4,4'-trichloro-2'-hydroxydiphenyl ether is present in proportions of about 0.02% to about 0.03%, said percentages being by weight of said compatible detergent base.

11. A process for sanitizing a fabric comprising contacting said fabric having thereon *S. aureus* cells with a nonionic detergent and a mixture of a 2-alkyl-2-imidazoline wherein the alkyl group has 9–17 carbon atoms and a bacteriostatic halogenated compound selected from the group consisting of 4',5-dibromosalicylanilide, 3,4',5-tribromosalicylanilide, 2,4,4'-trichloro-2'-hydroxydiphenyl ether and mixtures thereof, said halogenated salicylanilide being present in proportions of about 0.005 to about 0.4 part, and said 2,4,4'-trichloro-2'-hydroxydiphenyl ether being present in proportions of about 0.005 to about 0.03 part, for each 0.5 to 5 parts of said 2-alkyl-2-imidazoline, by weight, the percentage level of said mixture being sufficient to provide antibacterial effectiveness to said fabric.

12. The process of claim 11 wherein said mixture is in aqueous solution.

13. The process of claim 12 wherein said 2-alkyl-2-imidazoline is 2-tridecyl-2-imidazoline and wherein the concentration thereof is about 13 ppm to about 60 ppm, by weight of said solution, and wherein the concentration of said bacteriostatic halogenated compound is about 0.1 ppm to about 40 ppm by weight of said solution.

* * * * *